(12) United States Patent
Feng et al.

(10) Patent No.: US 7,329,860 B2
(45) Date of Patent: Feb. 12, 2008

(54) CONFOCAL IMAGING METHODS AND APPARATUS

(75) Inventors: Wenyi Feng, San Diego, CA (US); Theofilos Kotseroglou, Menlo Park, CA (US); Mark Wang, San Diego, CA (US); Alexander Triener, San Diego, CA (US); Diping Che, San Diego, CA (US); Robert Kain, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 82 days.

(21) Appl. No.: 11/286,309

(22) Filed: Nov. 23, 2005

(65) Prior Publication Data

US 2007/0114362 A1    May 24, 2007

(51) Int. Cl.
*H01L 27/00* (2006.01)
(52) U.S. Cl. ............... 250/234; 250/458.1; 250/459.1
(58) Field of Classification Search ........ 250/234–235, 250/208.1, 208.2, 458.1, 459.1, 586
See application file for complete search history.

(56) References Cited

U.S. PATENT DOCUMENTS

| | | | |
|---|---|---|---|
| 4,204,230 A | 5/1980 | Sprague | |
| 4,382,267 A | 5/1983 | Angle | |
| 4,700,298 A | 10/1987 | Palcic et al. | |
| 4,826,299 A | 5/1989 | Powell | |
| 4,845,552 A | 7/1989 | Jaggi et al. | |
| 4,877,326 A | 10/1989 | Chadwick et al. | |
| 5,159,199 A | 10/1992 | LaBaw | |
| 5,173,748 A | 12/1992 | Bilhorn | |
| 5,528,050 A | 6/1996 | Miller et al. | |
| 5,578,818 A | 11/1996 | Kain et al. | |
| 5,585,639 A | 12/1996 | Dorsel et al. | |
| 5,629,808 A | 5/1997 | Powell | |
| 5,719,391 A | 2/1998 | Kain | |

(Continued)

FOREIGN PATENT DOCUMENTS

EP    1 586 931    10/2005

(Continued)

OTHER PUBLICATIONS

Benedetti, P.A. et al., "Confocal-line microscopy," Journal of Microscopy, 165:119-129 (1992).

(Continued)

*Primary Examiner*—John R. Lee
(74) *Attorney, Agent, or Firm*—John T. Murphy

(57) ABSTRACT

The invention provides imaging apparatus and methods useful for obtaining a high resolution image of a sample at rapid scan rates. A rectangular detector array having a horizontal dimension that is longer than the vertical dimension can be used along with imaging optics positioned to direct a rectangular image of a portion of a sample to the rectangular detector array. A scanning device can be configured to scan the sample in a scan-axis dimension, wherein the vertical dimension for the rectangular detector array and the shorter of the two rectangular dimensions for the image are in the scan-axis dimension, and wherein the vertical dimension for the rectangular detector array is short enough to achieve confocality in a single axis.

46 Claims, 12 Drawing Sheets

U.S. PATENT DOCUMENTS

| | | |
|---|---|---|
| 5,754,291 A | 5/1998 | Kain |
| 5,782,770 A | 7/1998 | Mooradian et al. |
| 5,837,475 A | 11/1998 | Dorsel et al. |
| 5,847,400 A | 12/1998 | Kain et al. |
| 5,945,679 A | 8/1999 | Dorsel et al. |
| 5,981,956 A | 11/1999 | Stern |
| 5,998,796 A | 12/1999 | Liu et al. |
| 6,025,601 A | 2/2000 | Trulson et al. |
| 6,043,506 A | 3/2000 | Heffelinger et al. |
| 6,043,880 A | 3/2000 | Andrews et al. |
| 6,118,127 A | 9/2000 | Liu et al. |
| 6,134,002 A | 10/2000 | Stimson et al. |
| 6,160,618 A | 12/2000 | Garner |
| 6,177,990 B1 | 1/2001 | Kain et al. |
| 6,207,960 B1 | 3/2001 | Stern |
| 6,225,625 B1 | 5/2001 | Pirrung et al. |
| 6,229,635 B1 | 5/2001 | Wulf |
| 6,245,507 B1 | 6/2001 | Bogdanov |
| 6,252,236 B1 | 6/2001 | Trulson et al. |
| 6,309,601 B1 | 10/2001 | Juncosa et al. |
| 6,371,370 B2 | 4/2002 | Sadler et al. |
| 6,388,788 B1 | 5/2002 | Harris et al. |
| 6,400,487 B1 | 6/2002 | Harris et al. |
| 6,403,957 B1 | 6/2002 | Fodor et al. |
| 6,441,379 B1 | 8/2002 | Osgood et al. |
| 6,495,363 B2 | 12/2002 | Bogdanov |
| 6,545,264 B1 | 4/2003 | Stern |
| 6,590,689 B1 | 7/2003 | Dorsel |
| 6,592,036 B2 | 7/2003 | Sadler et al. |
| 6,597,000 B2 | 7/2003 | Stern |
| 6,650,411 B2 | 11/2003 | Odoy et al. |
| 6,678,048 B1 | 1/2004 | Rienstra et al. |
| 6,687,000 B1 | 2/2004 | White |
| 6,741,344 B1 | 5/2004 | Stern et al. |
| 6,813,018 B2 | 11/2004 | Richman |
| 6,825,930 B2 | 11/2004 | Cronin et al. |
| 6,838,650 B1 | 1/2005 | Toh |
| 6,902,112 B2 | 6/2005 | Sadler et al. |
| 2002/0030811 A1 | 3/2002 | Schindler |
| 2004/0140417 A1* | 7/2004 | Karin .................. 250/208.1 |
| 2005/0057749 A1* | 3/2005 | Dietz et al. ............. 356/318 |
| 2005/0161593 A1* | 7/2005 | Kitahara ................ 250/234 |
| 2007/0132998 A1* | 6/2007 | Tang et al. ............. 356/417 |

FOREIGN PATENT DOCUMENTS

| | | |
|---|---|---|
| WO | WO 99/47963 | 9/1999 |
| WO | WO 02/075292 | 9/2002 |
| WO | PCT/US2006/045058 | 3/2007 |

OTHER PUBLICATIONS

Benedetti, P.A. et al., "Achieving confocal-point performance in confocal-line microscopy," Bioimaging, 2:122-130 (1994).

Bewsher, A. et al., "Design on single-element laser-beam shape projectors," Applied Optics, 35:1654-1658 (1996).

Boas, G., "Scanning system offers high-throughput bioanalysis," Biophotonics International, 50-54 (2004).

Christensen, K. et al., "Hyperspectral Raman Microscopic Imaging Using Powell Lens Line Illumination," Applied Spectorscopy, 52:1145-1147 (1998).

Evangelista, V. et al., "Confocal-line optical microscopy," Proceedings of SPIE, 1319:464-465 (1990).

Global-Lasertech homepage [online], [retrieved on May 4, 2006]. Retrieved from the Global-Lasertech website using internet <URL: http://www.global-lasertech.co.uk>.

Hesse, J. et al., "Single-Molecule Reader for High-Throughput Bioanalysis," Analytical Chemistry, 76:5960-5964 (2004).

Im, K. et al., "Simple high-speed confocal line-scanning microscope," Optics Express, 13:5151-5156 (2005).

Jacak, J. et al., "Ultra-sensitive DNA detection on microarrays," SPIE, 5699:442-449 (2005).

Powell, I., "Design of a laser beam line expander," Applied Optics, 26:3705-3709 (1987).

Schultz, R. et al., "Hyperspectral Imaging: A Novel Approach For Microscopic Analysis," Cytometry, 43:239-247 (2001).

Sinclair, M. et al., "Design, construction, characterization, and application of a hyperspectral microarray scanner," Applied Optics, 43:2079-2088 (2004).

Sonnleitner, M. et al., "High-throughput scanning with single-molecule sensitivity," SPIE, 5699:202-210 (2005).

SPECIM Spectral Camera User Manual [online], [retrieved on May 3, 2006]. Retrieved from the Specim website using internet <URL: http://www.specim.fi/pdf/User_Manual_1_1.pdf>.

* cited by examiner

Fig. 15
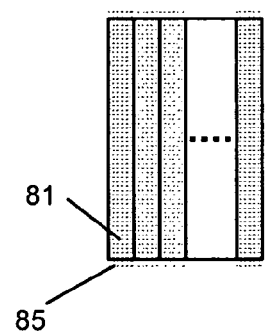
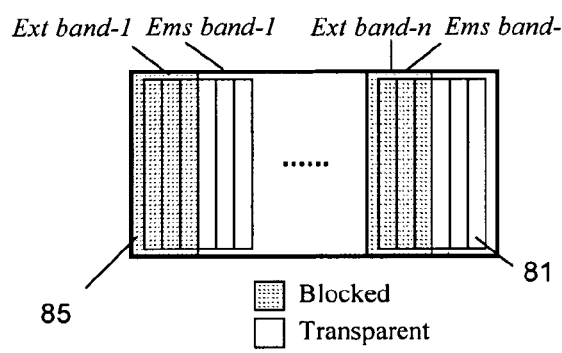
Fig. 16(a)
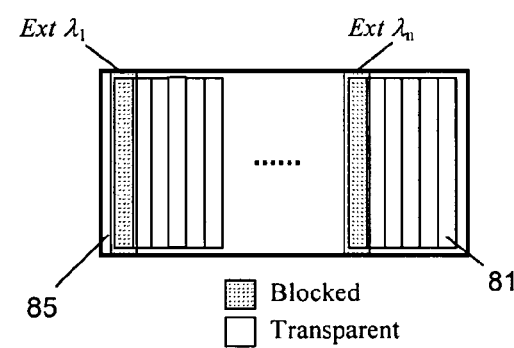
Fig. 16(b)

CONFOCAL IMAGING METHODS AND APPARATUS

BACKGROUND OF THE INVENTION

The present invention relates generally to the field of optical imaging. Specifically, the present invention relates to imaging systems for use in detecting microarrays.

Light microscopes provide a powerful tool for investigating samples at submicron resolution. For example, in biology and medicine, appropriate molecular tags, such as fluorescent and immunofluorescent tags, are used to label individual molecules and unique signals from the tags are detected by light microscope to identify their presence. Detection at submicron resolution allows not only determination of the presence of tagged molecules, but also their location in and around cells or tissues.

Two conflicting goals of light microscopy inspection systems concern providing high speed imaging and high resolution imaging. Typically, the resolution of a light microscope is inversely proportional to the imaging speed. Thus, greater resolution is often achieved at the cost of lower inspection rate. One technique to accommodate the aforementioned conflict is to selectively choose the resolution of the system according to specifics of the sample being observed or other conditions of the experiment. Thus, one can use lower resolution to achieve higher speeds while searching for an area of interest in a sample and then once a location of interest is found, imaging can be carried out at higher resolution, albeit at the cost of increasing the time of acquisition for the image.

Significant advances have been made in the ability of microscopes to investigate samples in three dimensions. The advent of confocal microscopes and improvements gained through related technology, allow a discrete point in 3-dimensional space to be detected at high resolution while rejecting unwanted signal from the volume around that point. Scanning confocal microscopy can be carried out to effectively move the point of detection through the sample and collect signal from each point to reconstruct an accurate 3-dimensional image of the sample.

Technology developed for light microscopy has been applied to other fields of image detection as well. For example, the technology has been used to obtain images of microarrays containing thousands of molecular probes attached to the surface of a substrate. Imaging of the surface of the microarrays after exposure to a biological sample of interest allows thousands of target molecules to be evaluated simultaneously, thereby providing vast amounts of information about the sample. For example, microarrays can be used to determine the number and types of genes that are expressed under particular conditions, which can in turn provide a holistic view of the biological response to the condition. Furthermore, similarities and differences between the genetic make-up of individuals can be evaluated using microarrays such that the genetic basis for particular traits can be determined. Information about the gene expression responses and genetic make-up of individuals can be used for diagnostic and prognostic purposes, for example, to determine susceptibility to a certain disease or response to a particular drug.

Although microarray detection has benefited from advances in light microscopy, there are a number of areas that have not been addressed adequately in regard to microarray imaging. In particular, advances directed to increasing image resolution and collection efficiency in light microscopy have come about by improving 3-dimensional confocal detection and altering magnification levels. However, typically array detection is carried out in only 2-dimensions and at a fixed magnification level. Furthermore, many of the advances in high resolution light microscopy have favored improvements in resolution over scan speed. These advances are favorable for imaging small samples, on the order of one or a few biological cells; however, the advances have not necessarily benefited high resolution scanning of substantially larger samples such as microarrays.

Thus, there exists a need for scanning devices and methods that allow imaging of microarrays and other 2-dimensional substrates at high resolution and at high speed. The present invention satisfies this need and provides other advantages as well.

BRIEF SUMMARY OF THE INVENTION

The invention provides an imaging apparatus. The imaging apparatus can include (a) a radiation source positioned to send excitation radiation to at least a portion of a sample region; (b) a rectangular detector array; (c) imaging optics positioned to direct a rectangular image of the portion to the rectangular detector array; and (d) a scanning device configured to scan the sample region in a scan-axis dimension, whereby the portion of the sample region that forms a rectangular image at the rectangular detector array is changed, wherein the shorter of the two rectangular dimensions for the rectangular detector array and the shorter of the two rectangular dimensions for the image are in the scan-axis dimension, and wherein the shorter of the two rectangular dimensions for the rectangular detector array is short enough to achieve confocality in a single axis of the rectangular detector array, wherein the single axis is the shorter of the two rectangular dimensions for the rectangular detector array.

The invention further provides a method of obtaining an image of a sample. The method can include the steps of (a) contacting at least a first portion of a sample with excitation radiation under conditions wherein radiation is emanated from the first portion; (b) directing the radiation emanated from the first portion to form a rectangular image of the first portion at a rectangular detector array; and (c) scanning the sample region in a scan-axis dimension, thereby repeating steps (a) and (b) to form a rectangular image of a second portion of the sample at the rectangular detector array, wherein the shorter of the two rectangular dimensions for the rectangular detector array and the shorter of the two rectangular dimensions for the images are in the scan-axis dimension, and wherein the shorter of the two rectangular dimensions for the rectangular detector array is short enough to achieve confocality in a single axis of the rectangular detector array, wherein the single axis is the shorter of the two rectangular dimensions for the rectangular detector array.

The invention also provides a method of configuring a scanner to achieve confocality in a single axis. The method can include the steps of (a) providing an apparatus having (i) a radiation source positioned to send excitation radiation to at least a portion of a sample region; (ii) a rectangular detector array; (iii) imaging optics positioned to direct a rectangular image of the portion to the rectangular detector array; and (iv) a scanning device configured to scan the sample region in a scan-axis dimension, whereby the portion of the sample region that forms a rectangular image at the rectangular detector array is changed, wherein the shorter of the two rectangular dimensions for the rectangular detector array and the shorter of the two rectangular dimensions for the image are in the scan-axis dimension; and (b) positioning the rectangular detector array or the imaging optics to restrict the shorter of the two rectangular dimensions for the rectangular detector array to be short enough to achieve confocality in a single axis of the rectangular detector array, wherein the single axis is the shorter of the two rectangular dimensions for the rectangular detector array. The methods can be carried out using the apparatus described in further detail below. However, it will be understood that the method steps exemplified below with regard to particular apparatus can also be carried out using an alternative apparatus.

BRIEF DESCRIPTION OF THE DRAWINGS

FIG. 15 is a block diagram of a line-scan imaging detector.

FIGS. 16(a)-(b) are block diagrams of line-scan imaging detectors.

DETAILED DESCRIPTION OF THE INVENTION

Figure 1:
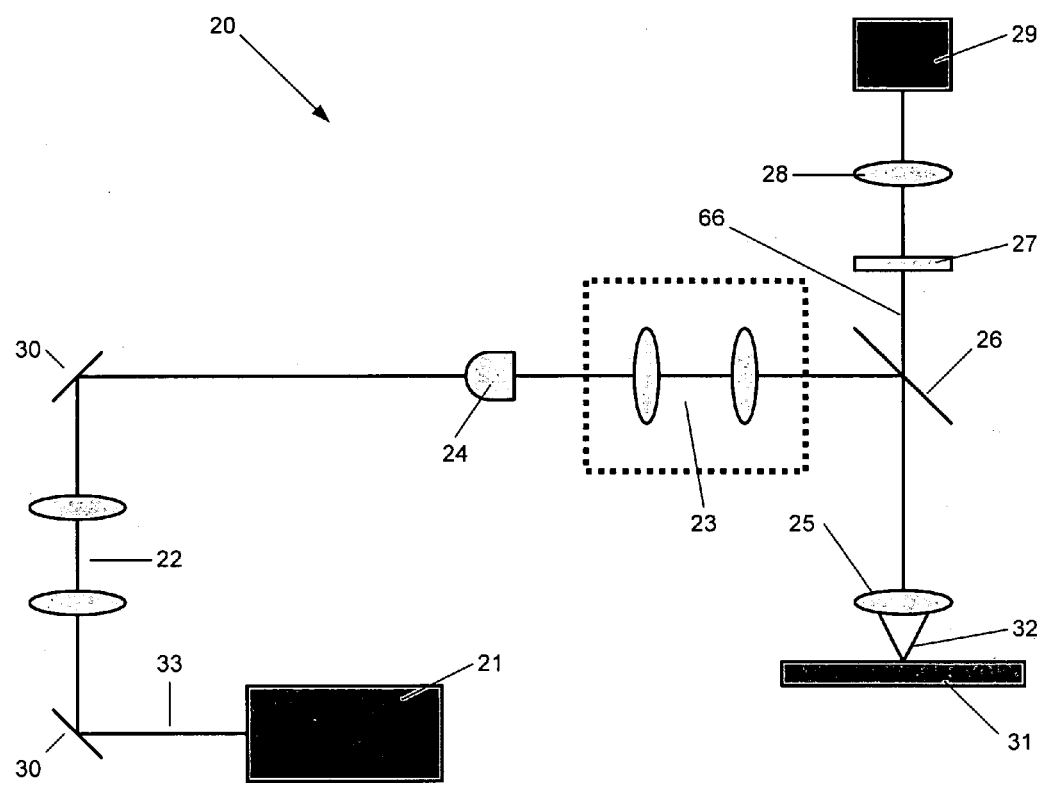
FIG. 1 is a block diagram of a line scan imaging apparatus.

The present invention provides an image scanning system and architecture having rapid scan times while maintaining high resolution and image quality. These and other advantages result from configuring a detector array to achieve confocality in the scanning axis by restricting the scan-axis dimension of the detector array. As set forth in further detail below, an apparatus of the invention can be configured to achieve confocality in a single axis of a detector array such that confocality only occurs in that dimension. Thus, in contrast to typical confocal systems where confocality is achieved in two dimensions, an apparatus of the invention can be configured such that confocality is not achieved in more than one dimension.

The detector array can have rectangular dimensions such that the shorter dimension of the detector is in the scan-axis dimension. Imaging optics can be placed to direct a rectangular image of a sample region to the detector array such that the shorter dimension of the image is also in the scan-axis dimension. In this way, the detector array forms a virtual slit. A virtual slit configuration provides several advantages over the use of a typical slit placed in front of a detector. For example, configuring a detector array as a virtual slit reduces the number of unused array elements compared to a configuration in which a detector array, having standard dimensions, is used with a slit. Reducing the number of unused elements increases efficiency of data acquisition and reduces image processing time. Furthermore, using a virtual slit allows both the detector and slit to be at the focal plane of the projection lens eliminating any focus compromise of either position or the requirement for a relay lens between the slit and detector.

A detector array configured to have a virtual slit is particularly useful when employed in an imaging apparatus that is further configured to direct a radiation line to a sample. The radiation line can have rectangular dimensions in which the shorter dimension is short enough to achieve confocality in a single axis corresponding to the shorter dimension of the detector array. Thus, confocality can be achieved for excitation, detection or both. An instrument can be configured to limit excitation error in the confocal axis such that predominantly all of the excitation radiation is contained within a spot comparable with the resolution of the instrument.

An apparatus that includes a detector array forming a virtual slit can be configured to obtain an image of the sample at high resolution, for example, in the low micron to submicron range. In particular embodiments, an image can be obtained at a Rayleigh resolution between 0.2 and 10 micrometers. Furthermore, the ratio of the shorter of the two rectangular dimensions for the rectangular detector array and the product of the Rayleigh resolution of the imaging optics multiplied by the magnification of the imaging optics can be used to determine the size and dimensions of the virtual slit for achieving confocality in a single axis. If desired, the ratio of the shorter of two rectangular dimensions for a radiation line to the Rayleigh resolution of the imaging optics can be selected to achieve confocality in a single axis.

Accordingly, an imaging apparatus of the invention can be configured to have resolution along the length of the line perpendicular to the scan axis that is matched to the system resolution. For example in a CCD device, 4000 CCD elements can be used along the length of a 2 mm radiation line (the horizontal axis) resulting in a 0.5 µm pixel resolution at a sample. The number of CCD elements "n" in the direction perpendicular to the radiation line (the vertical axis) can be chosen to collect substantially all of the emitted radiation while reducing the amount of unwanted background radiation collected.

An imaging apparatus of the invention can be further configured such that all pixel elements in the vertical axis are collected in a common "bin" and read out as a single value. Advantages of the binning approach compared to a typical Time Delay Integration (TDI) design are that the readout rate can be reduced by a factor of "n", the system has confocality in one axis, and the tolerance of the synchronization timing of the readout with the y-stage movement can be reduced. It will be understood that a TDI design can be configured to have a virtual slit by limiting the number of vertical pixels. An additional, advantage over system designs where n=1 are that the collection efficiency of the system can be increased and the sensitivity to small optical alignment drifts can be decreased.

Definitions

As used herein, the term "radiation source" is intended to mean an origin or generator of propagated electromagnetic energy. The term can include an illumination source producing electromagnetic radiation in the ultra violet (UV) range (about 200 to 390 nm), visible (VIS) range (about 390 to 770 nm), or infrared (IR) range (about 0.77 to 25 microns), or other range of the electromagnetic spectrum. A radiation source can include, for example, a lamp such as an arc lamp or quartz halogen lamp, or a laser such as a solid state laser or a gas laser.

As used herein, the term "excitation radiation" is intended to mean electromagnetic energy propagated toward a sample or sample region. Excitation radiation can be in a form to induce any of a variety of responses from a sample including, but not limited to, absorption of energy, reflection, fluorescence emission or luminescence.

As used herein, the term "sample region" is intended to mean a location that is to be detected. The location can be, for example, in, on or proximal to a support device that is configured to support or contain an object to be detected. A sample can occupy a sample region permanently or temporarily such that the sample can be removed from the sample region. For example a sample region can be a location on or near a translation stage, the location being occupied by a microarray when placed on the translation stage.

As used herein, the term "detector array" is intended to mean a device or apparatus having several elements that convert the energy of contacted photons into an electrical response. An exemplary detector array is a charge coupled device (CCD), wherein the elements are photosensitive charge collection sites that accumulate charge in response to impinging photons. Further examples of detector arrays include, without limitation, a complementary metal oxide semiconductor (CMOS) detector array, avalanche photo-diode (APD) detector array, or a Geiger-mode photon counter detector array. The elements of a detector array can have any of a variety of arrangements. For example, a rectangular detector array has elements in a 2-dimensional, orthogonal arrangement in which a first dimension, referred to as the "horizontal" dimension is longer than a second dimension referred to as the "vertical" dimension. A square detector array has elements in a 2-dimensional, orthogonal arrangement in which the first and second dimensions of the arrangement are the same length.

As used herein, the term "rectangular image" is intended to mean an optically formed representation of a sample, or portion of the sample, that occurs within a 2-dimensional, orthogonal region having a horizontal dimension that is longer than the vertical dimension. The rectangular image can represent the entirety of an image emanating from a sample region or, alternatively, can be a rectangular portion of a larger image, the larger image having any of a variety of shapes.

As used herein, the term "scanning device" is intended to mean a device capable of sequentially detecting different portions of a sample. A scanning device can operate, by changing the position of one or more component of a detection apparatus including, for example, a sample, radiation source, optical device that directs excitation radiation to a sample, optical device that directs radiation emanating from a sample, or detector array. Exemplary scanning devices include, but are not limited to a galvanometer configured to move a beam or line of radiation across a sample or a translation stage configured to move a sample across a beam or line of radiation.

As used herein, the term "Rayleigh resolution" is $R_R$ in the following equation $$R_R = ((1.22)(\lambda)(f))/D \qquad \text{Equation 1}$$

wherein $\lambda$ is wavelength, f is focal length and D is distance between two objects that are detected. The term is intended to be consistent with its use in the art of optics, for example, as set forth in Hecht, *Optics*, 4$^{th}$ ed., Addison Wesley, Boston Mass. (2001), which is hereby incorporated by reference.

As used herein, the term "magnification" is intended to mean the ratio of the size of an object to the size of an image of the object. For example, magnification can be determined from the ratio of the size of sample region (i.e. the object) to the size of an image of the sample region at a detector array. In systems including an objective and projection lens, magnification can be determined from the ratio of focal length of the objective to back focal length of the projection lens.

As used herein, the term "radiation line" is intended to mean a collection of electromagnetic waves or particles propagated in a uniform direction, wherein the 2-dimensional cross section orthogonal to the direction of propagation is rectangular or oblong. Exemplary 2-dimensional cross sections of a radiation line include, but are not limited to, a rectangular, elliptical, or oval shape. The cross sectional width of a radiation line can have one or both dimensions in a range of, for example, about 0.05 µm to about 10 µm. For example, a dimension of the radiation line can be at least about 0.05 µm, 0.1 µm, 0.5 µm, 1 µm, 5 µm or 10 µm. Furthermore, a dimension of a radiation line can be, for example, at most about 0.1 µm, 0.5 µm, 1 µm, 5 µm or 10 µm. It will be understood that these dimensions are merely exemplary and radiation lines having other dimensions can be used if desired.

As used herein, the term "line generator" is intended to mean an optical element that is configured to generate a diffraction-limited or near diffraction-limited radiation line in the plane perpendicular to the optical axis of propagation with a substantially uniform intensity distribution along the horizontal axis of the line. Exemplary line generators include, but are not limited to, a one dimensional diffuser having angular uniformity, cylindrical microlens array, diffractive element or aspheric refractive lens such as a Powell lens. The one dimensional diffuser having angular uniformity or cylindrical microlens array can be placed to direct radiation to a condenser.

As used herein, the term "beam splitter" is intended to mean an optical element that passes a first portion of a radiation beam and reflects a second portion of the beam. For example a beam splitter can be configured to selectively pass radiation in a first wavelength range and reflect radiation in a second, different radiation range. When used for fluorescence detection the beam splitter will typically reflect the shorter wavelength excitation radiation and transmit the longer wavelength emission radiation.

As used herein, the term "external pupil" is used in reference to an objective, where the entrance pupil to the back aperture of the objective is behind the physical dimensions of the objective in the excitation beam path.

As used herein, the term "expander" is intended to mean one or more optical elements configured to adjust the diameter and collimation of a radiation beam. For example, an expander can be configured to increase the diameter of a radiation beam by a desired amount such as at least 2 fold, 5 fold, 10 fold or more. Optical elements of an expander can include, for example, one or more mirrors or lenses.

As used herein, the term "projection lens" is intended to mean an optical element configured to transfer the image of an object to a detector. For example, a lens can be placed to transfer an image emanating from an objective lens to a detector array.

As used herein, the term "optical filter" is intended to mean a device for selectively passing or rejecting passage of radiation in a wavelength, polarization or frequency dependent manner. The term can include an interference filter in which multiple layers of dielectric materials pass or reflect radiation according to constructive or destructive interference between reflections from the various layers. Interference filters are also referred to in the art as dichroic filters, or dielectric filters. The term can include an absorptive filter which prevents passage of radiation having a selective wavelength or wavelength range by absorption. Absorptive filters include, for example, colored glass or liquid.

A filter used in the invention can have one or more particular filter transmission characteristics including, for example, bandpass, short pass and long pass. A band pass filter selectively passes radiation in a wavelength range defined by a center wavelength of maximum radiation transmission ($T_{max}$) and a bandwidth and blocks passage of radiation outside of this range. $T_{max}$ defines the percentage of radiation transmitted at the center wavelength. The bandwidth is typically described as the full width at half maximum (FWHM) which is the range of wavelengths passed by the filter at a transmission value that is half of $T_{max}$. A band pass filter useful in the invention can have a FWHM of 10 nanometers (nm), 20 nm, 30 nm, 40 nm or 50 nm. A long pass filter selectively passes higher wavelength radiation as defined by a $T_{max}$ and a cut on wavelength. The cut on wavelength is the wavelength at which radiation transmission is half of $T_{max}$; as wavelength increases above the cut on wavelength, transmission percentage increases and as wavelength decreases below the cut on wavelength transmission percentage decreases. A short pass filter selectively passes lower wavelength radiation as defined by a $T_{max}$ and a cut off wavelength. The cut off wavelength is the wavelength at which radiation transmission is half of $T_{max}$; as wavelength increases above the cut off wavelength, transmission percentage decreases and as wavelength decreases below the cut off wavelength transmission percentage increases. A filter of the invention can have a $T_{max}$ of 50-100%, 60-90% or 70-80%.

As used herein, the term "microarray" refers to a population of different probe molecules that are attached to one or more substrates such that the different probe molecules can be differentiated from each other according to relative location. An array can include different probe molecules, or populations of the probe molecules, that are each located at a different addressable location on a substrate. Alternatively, a microarray can include separate substrates each bearing a different probe molecule, or population of the probe molecules, that can be identified according to the locations of the substrates on a surface to which the substrates are attached or according to the locations of the substrates in a liquid. Exemplary arrays in which separate substrates are located on a surface include, without limitation, a Sentrix® Array or Sentrix® BeadChip Array available from Illumina®, Inc. (San Diego, Calif.) or others including beads in wells such as those described in U.S. Pat. Nos. 6,266,459, 6,355,431, 6,770,441, and 6,859,570; and PCT Publication No. WO 00/63437, each of which is hereby incorporated by reference. Other arrays having particles on a surface include those set forth in US 2005/0227252; WO 05/033681; and WO 04/024328.

Further examples of commercially available microarrays that can be used in the invention include, for example, an Affymetrix® GeneChip® microarray or other microarray synthesized in accordance with techniques sometimes referred to as VLSIPS™ (Very Large Scale Immobilized Polymer Synthesis) technologies as described, for example, in U.S. Pat. Nos. 5,324,633; 5,744,305; 5,451,683; 5,482, 867; 5,491,074; 5,624,711; 5,795,716; 5,831,070; 5,856, 101; 5,858,659; 5,874,219; 5,968,740; 5,974,164; 5,981, 185; 5,981,956; 6,025,601; 6,033,860; 6,090,555; 6,136, 269; 6,022,963; 6,083,697; 6,291,183; 6,309,831; 6,416, 949; 6,428,752 and 6,482,591, each of which is hereby incorporated by reference. A spotted microarray can also be used in a method of the invention. An exemplary spotted microarray is a CodeLink™ Array available from Amersham Biosciences. Another microarray that is useful in the invention is one that is manufactured using inkjet printing methods such as SurePrint™ Technology available from Agilent Technologies. Other microarrays that can be used in the invention include, without limitation, those described in Butte, *Nature Reviews Drug Discov.* 1:951-60 (2002) or U.S. Pat. Nos. 5,429,807; 5,436,327; 5,561,071; 5,583,211; 5,658,734; 5,837,858; 5,919,523; 6,287,768; 6,287,776; 6,288,220; 6,297,006; 6,291,193; and 6,514,751; and WO 93/17126; WO 95/35505, each of which is hereby incorporated by reference.

As used herein, the term "time delay integration" or "TDI" is intended to mean sequential detection of different portions of a sample by different subsets of elements of a detector array, wherein transfer of charge between the subsets of elements proceeds at a rate synchronized with and in the same direction as the apparent motion of the sample being imaged. For example, TDI can be carried out by scanning a sample such that a frame transfer device produces a continuous video image of the sample by means of a stack of linear arrays aligned with and synchronized to the apparent movement of the sample, whereby as the image moves from one line to the next, the stored charge moves along with it. Accumulation of charge can integrate during the entire time required for the row of charge to move from one end of the detector to the serial register (or to the storage area of the device, in the case of a frame transfer CCD).

As used herein, the term "collection arm" is intended to mean an optical component or set of optical components positioned to direct radiation from a sample region to a detector.

DESCRIPTION OF PARTICULAR EMBODIMENTS

Embodiments will be described below with reference to the accompanying drawings. It should be understood that the following description is intended to describe exemplary embodiments of the invention, and not to limit the invention.

The invention provides an imaging apparatus. The imaging apparatus can include (a) a radiation source positioned to send excitation radiation to at least a portion of a sample region; (b) a rectangular detector array; (c) imaging optics positioned to direct a rectangular image of the portion to the rectangular. detector array; and (d) a scanning device configured to scan the sample region in a scan-axis dimension, whereby the portion of the sample region that forms a rectangular image at the rectangular detector array is changed, wherein the shorter of the two rectangular dimensions for the rectangular detector array and the shorter of the two rectangular dimensions for the image are in the scan-axis dimension, and wherein the shorter of the two rectangular dimensions for the rectangular detector array is short enough to achieve confocality in a single axis of the rectangular detector array, wherein the single axis is the shorter of the two rectangular dimensions for the rectangular detector array.

The invention further provides a method of obtaining an image of a sample. The method can include the steps of (a) contacting at least a first portion of a sample with excitation radiation under conditions wherein radiation is emanated from the first portion; (b) directing the radiation emanated from the first portion to form a rectangular image of the first portion at a rectangular detector array; and (c) scanning the sample region in a scan-axis dimension, thereby repeating steps (a) and (b) to form a rectangular image of a second portion of the sample at the rectangular detector array, wherein the shorter of the two rectangular dimensions for the rectangular detector array and the shorter of the two rectangular dimensions for the images are in the scan-axis dimension, and wherein the shorter of the two rectangular dimensions for the rectangular detector array is short enough to achieve confocality in a single axis of the rectangular detector array, wherein the single axis is the shorter of the two rectangular dimensions for the rectangular detector array.

The invention also provides a method of configuring a scanner to achieve confocality in a single axis. The method can include the steps of (a) providing an apparatus having (i) a radiation source positioned to send excitation radiation to at least a portion of a sample region; (ii) a rectangular detector array; (iii) imaging optics positioned to direct a rectangular image of the portion to the rectangular detector array; and (iv) a scanning device configured to scan the sample region in a scan-axis dimension, whereby the portion of the sample region that forms a rectangular image at the rectangular detector array is changed, wherein the shorter of the two rectangular dimensions for the rectangular detector array and the shorter of the two rectangular dimensions for the image are in the scan-axis dimension; and (b) positioning the rectangular detector array or the imaging optics to restrict the shorter of the two rectangular dimensions for the rectangular detector array to be short enough to achieve confocality in a single axis of the rectangular detector array, wherein the single axis is the shorter of the two rectangular dimensions for the rectangular detector array. The methods can be carried out using the apparatus described in further detail below. However, it will be understood that the method steps exemplified below with regard to particular apparatus can also be carried out using an alternative apparatus.

FIG. 1 shows an embodiment 20 of a line-scan imaging system ("LIS"). The LIS 20 includes a radiation source 21, a first and second expander 22, 23, a line generator 24, an objective 25, a beam splitter 26, a filter 27, a projection lens 28 and a detector array 29. In addition, the LIS 20 includes several mirrors 30 for directing radiation.

Figure 2:
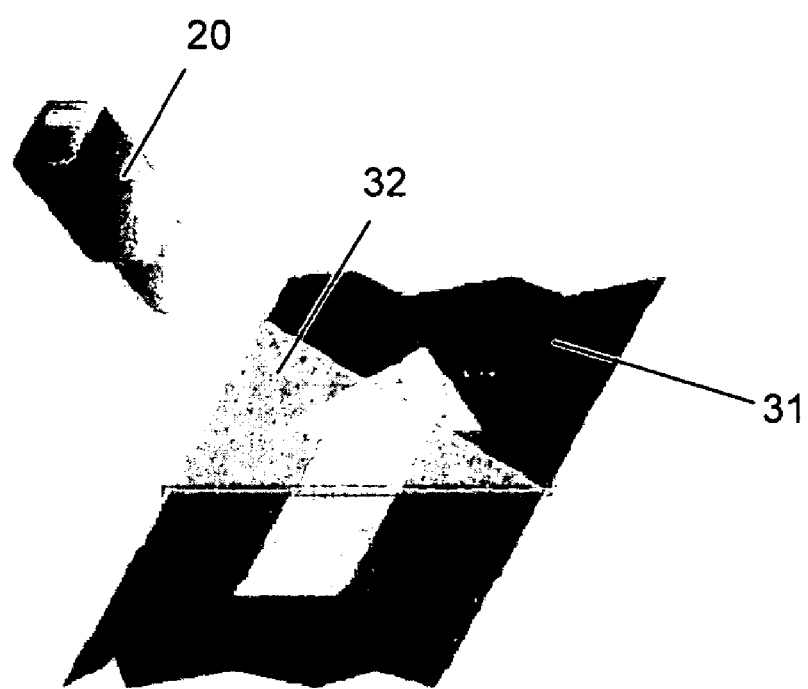
FIG. 2 is a conceptual diagram of an object being scanned by a line scan camera.

As shown in FIG. 2, the LIS 20 is configured to scan a sample region located at a sample stage 31 with a radiation line 32. The components of the LIS 20 are configured in such a way that the sample is scanned by a radiation line 32 that is substantially narrow and uniform. For example, the radiation line 32 can be 2 mm long in the longer dimension, referred to as the horizontal dimension, and less than 3 μm in width at its widest point in the vertical dimension. Specifically, the LIS 20 can be configured to continuously scan a stage containing a sample by moving the sample stage 31 along the vertical dimension as indicated by the arrow in FIG. 2. The portion of the sample excited by the scan line can form a rectangular image on the detector array 29 with the horizontal dimension of scan line 32 correlating with the horizontal dimension of the detector array 29. Accordingly, the sample is scanned past the imaging area of a detector array 29 along the vertical dimension.

Initially, a radiation source 21 produces an excitation beam 33, which is directed through an expander 22. According to one embodiment, the radiation source 21 is a laser. Other useful radiation sources include, for example, a lamp such as an arc lamp or quartz halogen lamp. Any of a variety of other radiation sources can be used as desired for exciting a sample at a particular wavelength. As desired for a particular application, radiation source 21 can generate radiation at various wavelengths including, for example, a wavelength in the UV, VIS or IR range. For example, an apparatus of the invention can include a laser that generates light at 405 nm, 488 nm, 532 nm or 633 nm.

Figure 3:
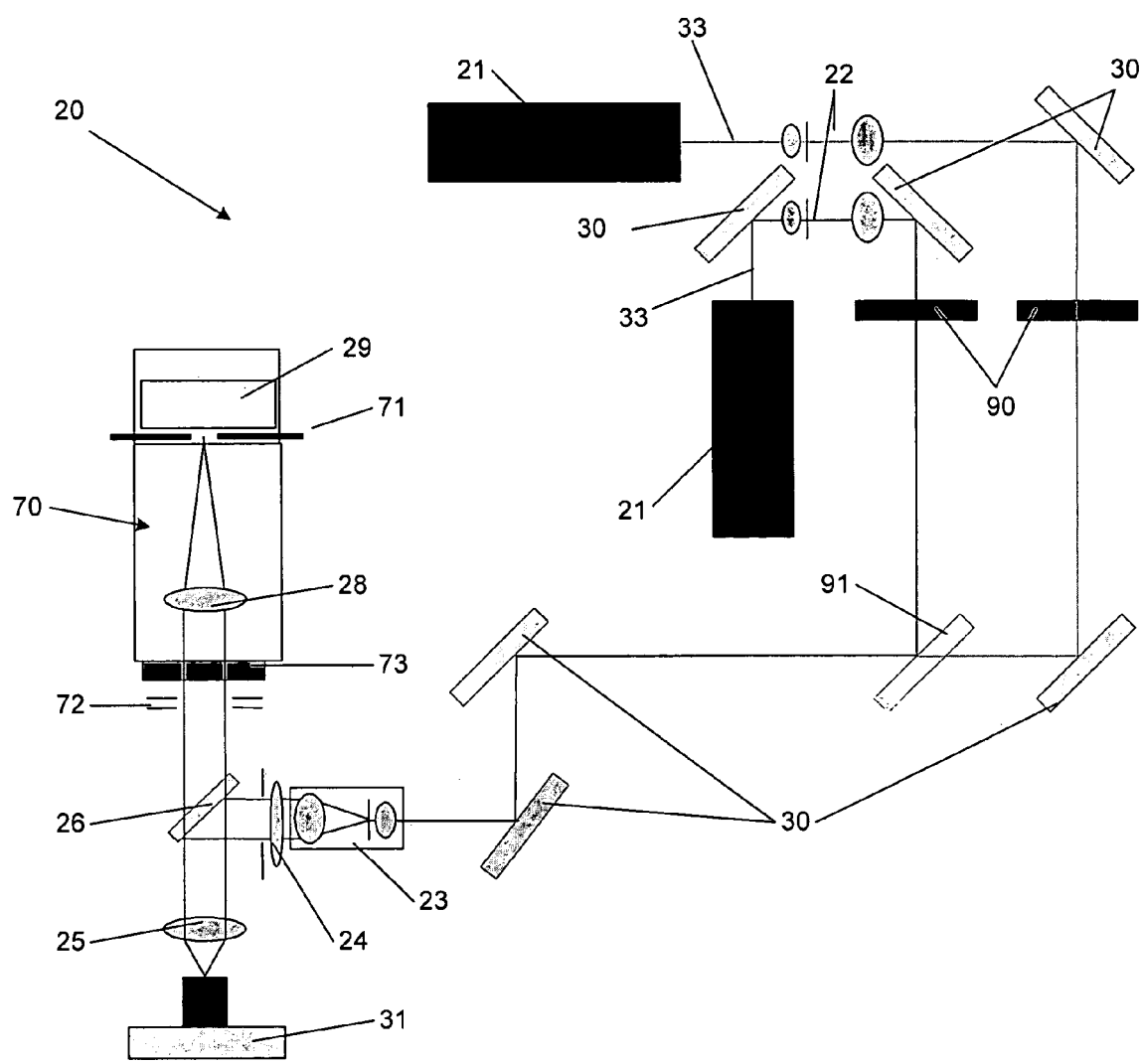
FIG. 3 is a block diagram of a line scan imaging apparatus.
Figure 4:
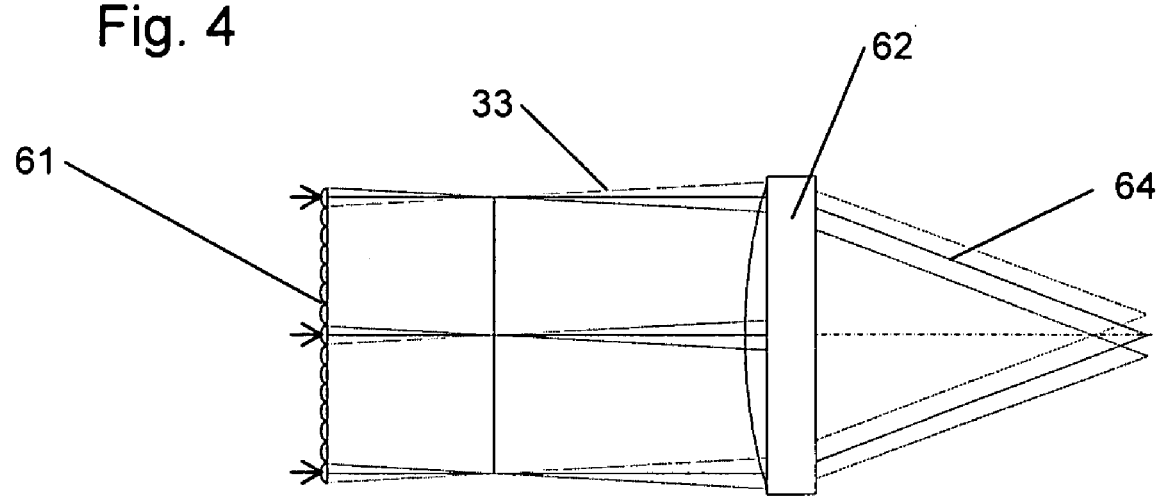
FIGS. 4 through 7 are perspective views of line generators.

As shown in FIG. 3, a LIS 20 can include more than one radiation source 21. The multiple radiation sources 21 can be lasers each capable of generating radiation at different wavelengths. The use of multiple radiation sources that generate radiation at different wavelengths can be useful, for example, in applications wherein a sample includes one or more fluorophores that produce different emission signals when excited at different wavelengths. Different emission signals can be collected simultaneously, for example, using multiple detection arms as set forth below in further detail. Alternatively or additionally, different emission signals can be collected sequentially following sequential excitation at different wavelengths. As shown in the example of FIG. 3, the excitation radiation 33 generated by each radiation source can pass through filters 90 and a radiation combiner 91 before being directed to an expander 23. The radiation source can include 2 or more lasers, for example, in applications where a sample is to be excited at multiple different wavelengths.

An apparatus of the invention can further include an expander positioned to receive excitation radiation from a radiation source and to send an expanded beam of the radiation to a line generator. Referring back to FIG. 1, in particular embodiments, the diameter of the excitation beam 33 generated by the radiation source 21 is approximately 1 mm in diameter. The first expander 22 is capable of expanding the diameter of the beam 33. For example, according to one embodiment, the expander 22 expands the excitation beam 33 to a diameter of 4 mm. Other useful beam expanders can bring the diameter of a radiation beam to at least about 0.5 mm, 1 mm, 2 mm, 5 mm, 10 mm, 15 mm, 20 mm or more.

An apparatus of the invention can further include a line generator positioned to receive excitation radiation and to send a radiation line to a sample region. Continuing with the exemplary embodiment shown in FIG. 1, after exiting the first expander 22, the excitation beam 33 can be directed through a line generator 24. A line generator 24 is inserted into the excitation radiation path to shape the excitation beam 33 such that the beam 33 is transformed from a beam of a fixed diameter to a line profile or radiation line as shown in FIG. 2. For example, the line generator 24 can transform an excitation beam 33 in the shape of a 1 μm diameter spot to a 2 mm×1 μm line profile at a sample region. Thus, the line generator 24 is configured to create a radiation line 32 at a sample region such as on the surface of the sample stage 31.

A line generator useful in the invention can include a diffractive element configured to generate a diffraction-limited line with uniform intensity distribution. For example a cylindrical micro-lens array and a condenser can be used. The cylindrical micro-lens array can be configured to focus excitation radiation onto the front focal plane of the condenser to generate a diffraction-limited line with uniform intensity distribution. A further example of a line generator is a one-dimensional diffuser having an angular uniformity and a condenser, wherein the one-dimensional diffuser is placed at the front focal plane of the condenser to generate a diffraction-limited line with uniform intensity distribution.

If desired, the line generator can further include an aspheric refractive lens to generate a diffraction-limited line with uniform intensity distribution. An exemplary aspheric refractive lens is a Powell lens.

In a particular embodiment, line generator 24 can be configured to receive an input excitation beam 33 having a diameter of 4 mm to obtain a fan angle of six degrees. Other useful configurations include, but are not limited to, those that receive an input excitation beam having a diameter of at most about 0.1 to 50 mm. A line generator can obtain a fan angle of at least about 0.1° to at most about 80°, full width. The beam diameter and fan angle can be selected to achieve a desired shape for a radiation line. Generally, the width of the radiation line depends upon beam diameter such that a larger beam diameter provides a wider radiation line in the vertical dimension and the length of the radiation line depends on the fan angle such that a larger fan angle provides a longer radiation line in the horizontal dimension. Typically, the line should appear to originate at the pupil of the objective, however this is not a requirement.

As set forth above, any of a variety of optical elements capable of generating a line can be placed in the optical path between a radiation source and a sample region to be irradiated. For example, an arc lamp focused on a slit and then collimated can be used to generate a line. A further example, is an edge emitting diode laser having an anamorphic beam which generates a line when focused. It will be understood that a radiation source used to irradiate a sample region can itself be capable of generating a line. Thus, a radiation source useful in the invention can include a line generator.

Any of a variety of methods and apparatus including, but not limited to those exemplified above, can be used to direct a radiation line to a sample region. The dimensions of the radiation line can be selected to achieve confocality in a single axis of a rectangular detector array. More specifically, the vertical dimension of the radiation line can be short enough to achieve confocality in the vertical dimension of the rectangular detector array.

A line generator of the invention is typically configured to produce a radiation line having a shape at a sample region that is rectangular or oblong. Exemplary shapes include, but are not limited to, a rectangular, elliptical, or oval shape. A line. generator can be configured to produce a radiation line having one or more of the properties set forth below.

A radiation line that contacts a sample region can have a ratio of the 1/e^2 width of the vertical dimension for the radiation line to the quotient of the vertical dimension for the rectangular detector array divided by the magnification of the imaging optics that results in confocality in one dimension. For example, the ratio can be at least about 0.5, 1, 1.5, 2, 3 or higher. An apparatus of the invention can be configured to have an upper end for the ratio that is at most about 2, 1.5, 1, 0.5 or lower. The ratio can be outside or inside the above ranges as desired including, for example, being in the range of 0.5 to 3.

A radiation line that contacts a sample region can have a ratio of the vertical dimension for the radiation line to the quotient of the vertical dimension for the rectangular detector array divided by the magnification of the imaging optics that results in confocality in one dimension. For example, the ratio can be at least about 0.1, 0.5, 1, 5, 10 or higher. The upper end of the ratio can be at most about 10, 5, 1, 0.5, 0.1 or lower. The ratio can be outside or inside the above ranges as desired including, for example, being in the range of 0.1 to 10.

Furthermore, the ratio of the vertical dimension for the radiation line to the Rayleigh resolution of the imaging optics can be at least about 0.1, 0.5 1, 5, 10 or higher. The upper end of the ratio can be at most about 10, 5, 1, 0.5, 0.1 or lower. The ratio can be outside or inside the above ranges as desired including, for example, being in the range of 0.1 to 10.

Although the invention is exemplified herein with regard to embodiments in which a sample region is contacted with a radiation line, it will be understood that the radiation that contacts a sample region can have other shapes including, for example, a square or circle.

An apparatus of the invention can include an objective positioned to receive radiation therethrough to illuminate a sample region. The objective can be further positioned to collect radiation emanating from a sample region and direct it to a detector array. Optionally, the apparatus can include a second expander positioned to receive the excitation radiation from the line generator and send an expanded beam of the radiation to the objective. The second expander can be further configured to decrease the field angle of the radiation line. For example, referring back to FIG. 1, after the excitation beam 33 passes through the line generator 24 and/or second expander 23, it is directed to an objective 25 by a beam splitter 26. In particular embodiments, the objective has an external pupil positioned to receive the radiation line therethrough to illuminate the sample region. Preferably, the beam splitter 26 is located near the entrance pupil of the objective lens 25. The beam splitter can be placed at an axial or lateral position relative to the objective. If desired, an objective can have a property of color correction, high numerical aperture, telecentricity, afocality at the backplane or a combination of such properties.

Continuing with the embodiment shown in FIG. 1, the beam splitter 26 directs the radiation line 32 to the objective 25. The objective 25 can be a microscope objective. Preferably, the objective 25 has a focal length of 20 mm. Accordingly, the objective 25 possesses a numerical aperture of 0.366. Further, the objective 25 has a field angle of +/−3 degrees and an entrance pupil having a 16 mm diameter. Preferably, the objective 25 is telecentric. Exemplary telecentric objective lenses useful in the invention include those that are described in U.S. Pat. No. 5,847,400, which is incorporated herein by reference.

In the exemplary embodiment of FIG. 1, a small region of the sample emits fluorescent light as a result of being exposed to the radiation line 32. The objective 25 collects the radiation emitted by the sample and forms a retro-beam 66. The objective 25 directs the retro-beam 66 along an identical path of the radiation line 32 in the opposite direction. The retro-beam 66 impinges on the beam splitter 26, which separates the radiation emitted by the sample from the excitation radiation 32. The beam splitter 26 directs the retro-beam 66 onto a projection lens 28 via a band pass filter 27. Thus, the beam splitter is positioned to separate the radiation line that is directed to a sample region from the radiation emanating from the sample region. The beam splitter is further placed to direct the radiation emanating from the sample region to a rectangular detector array.

As exemplified above, band pass filter 27 can be positioned to filter radiation emanating from a sample region, wherein the radiation emanating from the sample region forms a rectangular image that is directed to a rectangular detector array. In particular embodiments, an additional emission filter can be placed in the optical path between the sample region and rectangular detector array to replace or supplement band pass filter 27.

In particular embodiments, stage 31 is a translation stage. The translation stage can be configured to move the sample, thereby changing the relative positions of the rectangular image and the rectangular detector array in the scan-axis (vertical) dimension. Movement of the translation stage can be in one or more dimensions including, for example, one or both of the dimensions that are orthogonal to the direction of propagation for the radiation line and typically denoted as the x and y dimensions. In particular embodiments, the translation stage can be configured to move in the direction perpendicular to the scan axis for a detector array. A stage 31 useful in the invention can be further configured for movement in the dimension along which the radiation line propagates, typically denoted as the z dimension. Movement in the z dimension can be useful for focusing the apparatus.

As shown in FIGS. 1 and 3, the projection lens 28 is positioned below a line scan camera 29. The projection lens 28 is configured to provide sufficient optical quality along the field angle described by the radiation line 32. Preferably, the projection lens 28 has a focal length of 500 mm and a field angle of +/−3 degrees.

According to one embodiment of the invention, as shown in FIG. 3, the projection lens 28 is enclosed in a radiation collection arm 70. In addition to the projection lens 28, a line scan CCD camera 29 is also enclosed within the radiation collection arm 70. Light baffles 71 are positioned in close proximity to the line scan CCD camera 29 so that the amount of stray radiation entering the line scan CCD camera 29 is reduced. Additional baffles 72 and a filter wheel 73 are positioned near the end of the collection arm 70 opposite the line scan CCD camera 29. Only one radiation collection arm 70 is displayed in FIG. 3, but it is to be understood that the system can incorporate more than one radiation collection arm as described above.

A rectangular detector array of the invention can be configured to form a virtual slit as set forth previously herein. In particular embodiments, the size and dimensions of the virtual slit can be determined from the ratio of the vertical dimension for the rectangular detector array and the product of the Rayleigh resolution of the imaging optics multiplied by the magnification of the imaging optics. For example, the ratio of the vertical dimension for the rectangular detector array and the product of the Rayleigh resolution of the imaging optics multiplied by the magnification of the imaging optics can be in the range of 0.1 to 10 or in the range of 0.5 to 3. An apparatus of the invention can be configured to obtain an image of a sample at a desired or optimal Rayleigh resolution including, for example, a Rayleigh resolution between 0.2 and 10 micrometers.

In particular embodiments, the aspect ratio of the number of detection elements in a first dimension to the number of detection elements in the scan-axis dimension for a rectangular detector array can be greater than 2, 10, 20, 50, 100, 1000 or higher. For example, the line scan CCD camera 29 can be configured to capture, four thousand (4,000) pixels in the first dimension and n pixels in the scan-axis (vertical) dimension. The CCD line scan camera 29 can be designed such that the resolution along the length of the line is matched to the system resolution. In this case, the horizontal axis includes approximately 4,000 CCD elements along the length of a 2 mm radiation line 32, resulting in a 0.5 μm pixel resolution at the object. The number of CCD elements "n" in the direction perpendicular to the horizontal axis, also referred to as the vertical axis, can be chosen to collect substantially all of the emitted radiation while reducing the amount of background radiation collected. According to one embodiment of the invention, the CCD has 4096 pixels, each 12 μm in size. To image a 2 mm line to this size CCD requires a magnification of 25×. Accordingly, n can be in the range of six to eight pixels. The design architecture limits the excitation error in the confocal axis such that predominantly 100% of the excitation radiation is contained within a spot comparable with the resolution of the LIS 20. In this case, the spot size would be roughly 1.0 μm.

Although the apparatus has been exemplified above with regard to a CCD line scan camera, it will be understood that any of a variety of other detectors can be used including, but not limited to a detector array configured for TDI operation, a CMOS detector, APD detector, Geiger-mode photon counter or other detector set forth elsewhere herein.

As illustrated in FIGS. 4-9, a diffraction-limited line with uniform intensity distribution can be generated using a number of architectures. In one such embodiment, shown in FIG. 4, the line generator 24 can be formed with a cylindrical micro-lens array 61 and a condenser 62. A cylindrical micro-lens array 61 is used to focus the excitation beam 33 to the front focal plane of a condenser 62 in one dimension while leaving a second dimension unaffected. A diffraction-limited line 64 with uniform intensity distribution will be generated on the back focal plane of the condenser 62. The uniformity of the line is related to the number of cylindrical micro-lenses 61 that cover the entrance pupil of the condenser 62. The greater the number of cylindrical micro-lens arrays 61, the more uniform the line intensity distribution will be.

Figure 5:
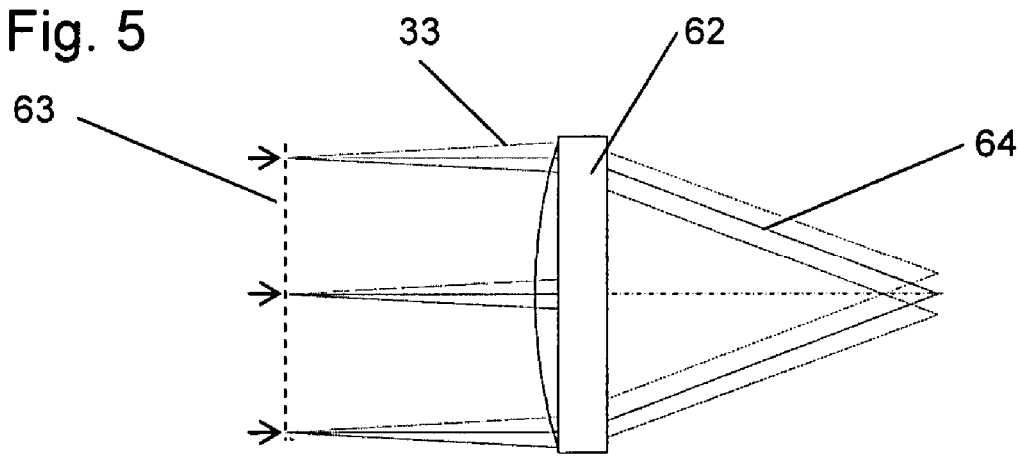

According to another embodiment and as shown in FIG. 5, the line generator 24 can be formed with a one-dimensional diffuser 63 and a condenser 62. A one-dimensional diffuser 63 having an angular uniformity is placed at the front focal plane of a condenser 62. The diffuser 63 fans the input collimated beam 33 in one dimension and leaves another dimension unaffected. A diffraction-limited line 64 with uniform intensity distribution will be generated on the back focal plane of the condenser 62. Since the diffuser 63 has angular uniformity, the generated line will be uniform.

In still another embodiment of the invention, an objective 25 is used as a condenser 62. Preferably, the objective lens 25 is a telecentric lens with an external pupil size of 15.75 mm. Preferably, this size is configured to match the diameter of the collimated input excitation beam 33. In addition, the input field angle of the lens is +/−3 degrees, which corresponds to a field view of 2 mm.

Figure 6:
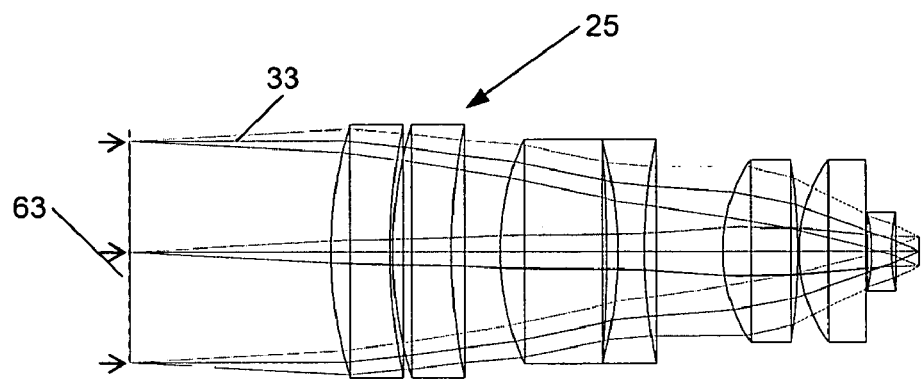

FIG. 6 shows a one-dimensional diffuser 63 in use with the objective 25 described above. As shown in FIG. 6, a one-dimensional diffuser 63 is placed at the pupil stop of the objective 25. The objective 25 diffuses the collimated input beam 33 to different angles in a certain range in one dimension and leaves another dimension unaffected. The diffuser 63 has angular uniformity, i.e. the intensities of beams diffused to different angles are the same. The lens 25 focuses the beam at each particular angle to a point in the line. The uniformity of the line is determined by the angular sensitivity of the diffuser 63. In addition, the length of radiation line 32 is determined by the fan angle of the diffuser 63. The larger the fan angle is, the longer the generated radiation line 32 will be. If the fan angle of the diffuser 63 is +/−3°, the generated line length will be 2 mm. Although the length of the radiation line 32 can be longer than 2 mm, a desired uniformity can be obtained by a line 2 mm in length.

Figure 7:
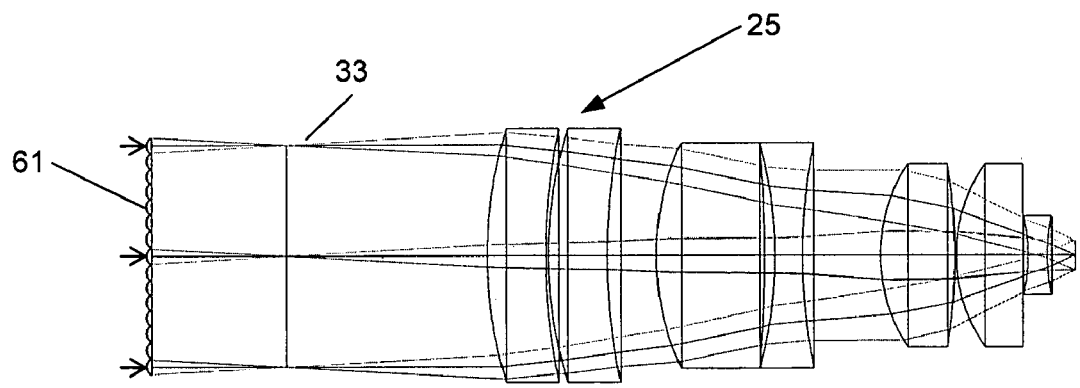

According to another embodiment, FIG. 7 shows a cylindrical micro-lens array 61 in use with the above-described objective 25. Each cylindrical micro-lens 61 samples a portion of the collimated input beam 33, focuses it to the pupil stop of the objective 25 in one dimension, and leaves the second dimension unaffected. The cylindrical micro-lens array 61 fans the beam 33 to different angles in a certain range in one dimension. The fan angle is determined by the f-number of the cylindrical micro-lenses 61. The objective lens 25 focuses the beam 33 at each angle to a point in the line. Since each point in the focused line gets contribution from all the cylindrical micro-lenses 61, the uniformity of the line is related to the number of cylindrical micro-lenses 61 that covers the entrance pupil of the objective lens 25. For example, according to one embodiment of the invention, 158 micro-lenses are used to cover the pupil stop in order to generate a uniform line excitation 32.

Figure 8:
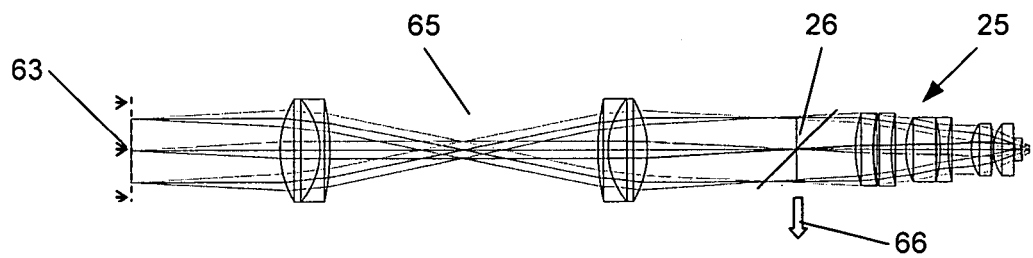
FIGS. 8 and 9 are perspective views of a line generator in a fluorescence imaging system.
Figure 9:
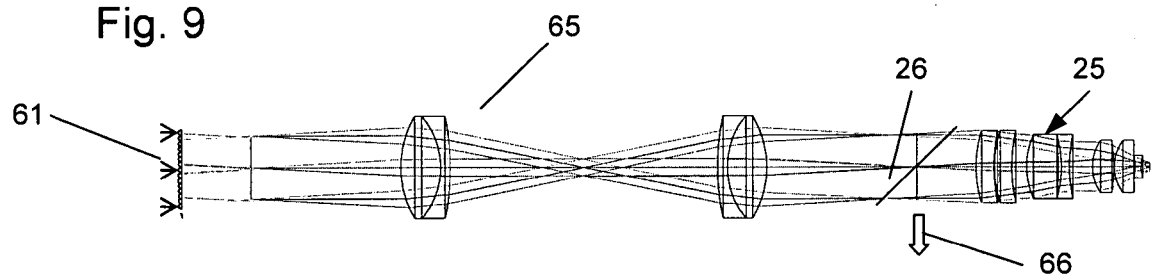

FIGS. 8 and 9 show additional embodiments of relay telescopes, configured for fluorescent imaging. A relay telescope 65 is positioned between the one-dimensional diffuser 63 (see FIG. 8) or cylindrical micro-lens array 61 (see FIG. 9) and a dichroic beam splitter 26. The dichroic beam splitter 26 is configured to separate the fluorescence imaging path (retro-beam) 66 from the excitation path 33.

A CCD camera or other detector array used in the invention can be configured for binning. Binning increases the detector array's sensitivity by summing the charges from multiple pixels in the array into one pixel. Exemplary types of binning that can be used include horizontal binning, vertical binning, or full binning. With horizontal binning, pairs of adjacent pixels in each line of a detector array are summed. With vertical binning, pairs of adjacent pixels from two lines in the array are summed. Full binning is a combination of horizontal and vertical binning in which four adjacent pixels are summed.

Figure 10A:
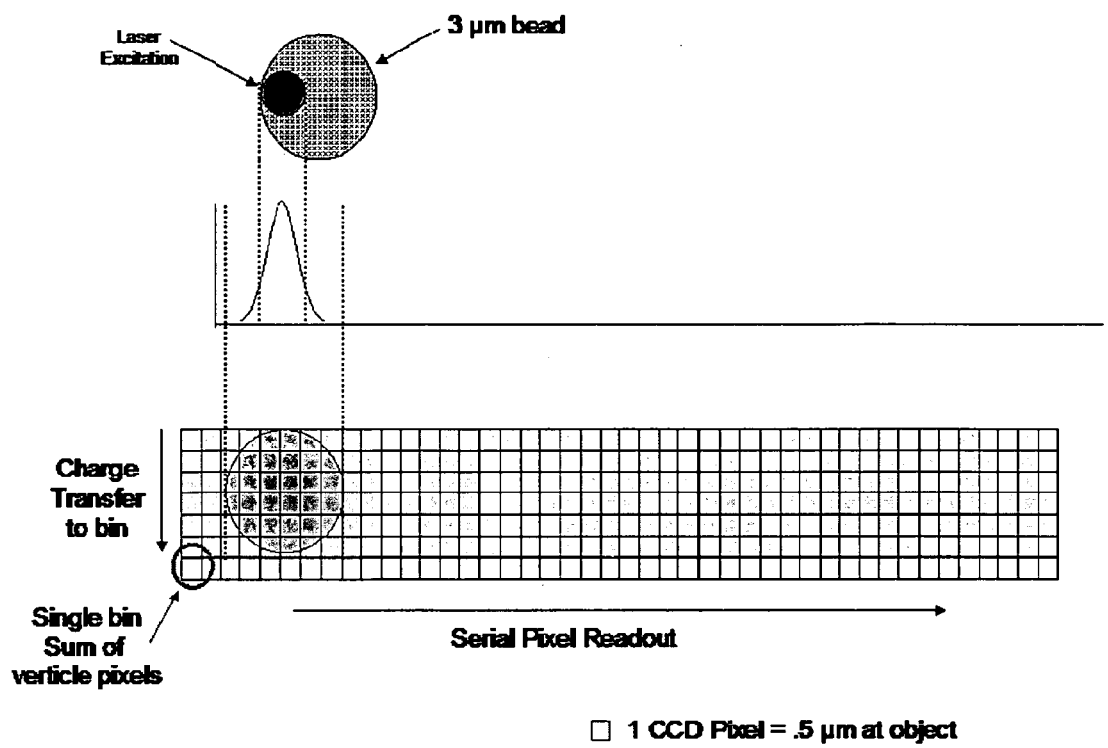
FIGS. 10(a)-(c) are diagrams showing the projection of a laser spot on a line scan camera and binning and TDI implementations.
Figure 10B:
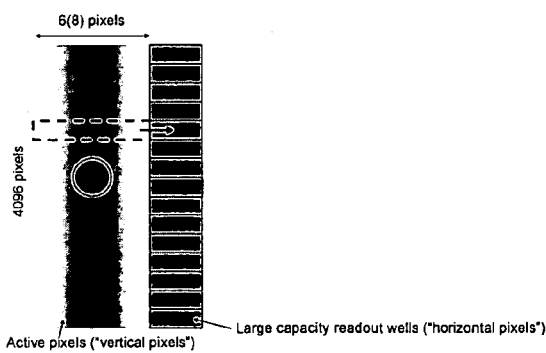
Figure 10C:
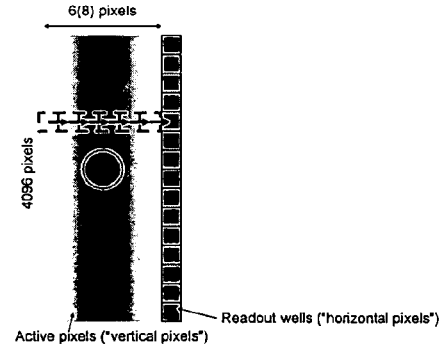

Binning in the invention can be carried out with larger sets of sensor elements. As illustrated in FIG. 10(*a*), the line scan CCD camera 29 and corresponding control electronics can be configured such that all pixel elements in the vertical axis are collected in a common bin and read out as a single value. Thus, binning need not be limited to adjacent pairs or adjacent groups of array elements. Accordingly, a set of more than 2 sensor elements, such as pixels of a CCD camera, can be binned even if the set includes non-adjacent sensor elements. Non-adjacent sensor elements occur, for example, in a linear arrangement of 3 sensor elements where the first and third elements are separated from each other by the intervening second sensor element.

As shown in FIG. 10(*b*), in binning, all of the pixels in a row are shifted out at once after a single integration time. The advantage of this approach, when used in an apparatus of the invention, is that compared to a common TDI design the readout rate is less sensitive to jitter. Furthermore, the apparatus would have confocality in one axis, and the tolerance of the synchronization timing of the readout with the y-stage movement would be reduced. FIG. 10(*b*) shows the projection of a 1 μm laser spot on a line scan CCD camera 29. The projection is symmetrical in both the x and y-axis. Limiting the number of CCD pixels to 6 in the vertical axis creates a virtual slit in that axis. The same effect can be achieved with a TDI camera, the main requirement is that the number of pixels in the vertical axis be optimized to pass a signal while also rejecting background noise. To achieve this, the laser spot size is set to match the resolution of the system in conjunction with limiting the number of vertical pixels.

An alternate embodiment of the invention uses a TDI design which limits the number of vertical pixels such that the virtual slit is still created. As shown in FIG. 10(*c*), in TDI, pixels are shifted in sync with the encoder output of the y-stage. Additionally, the advantage over system designs where n=1 are that the collection efficiency of the system would be increased and the sensitivity to small optical alignment drifts would be decreased. Exemplary TDI designs and methods that can be used in the invention are described in U.S. Pat. No. 5,754,291, which is incorporated herein by reference.

Figure 11:
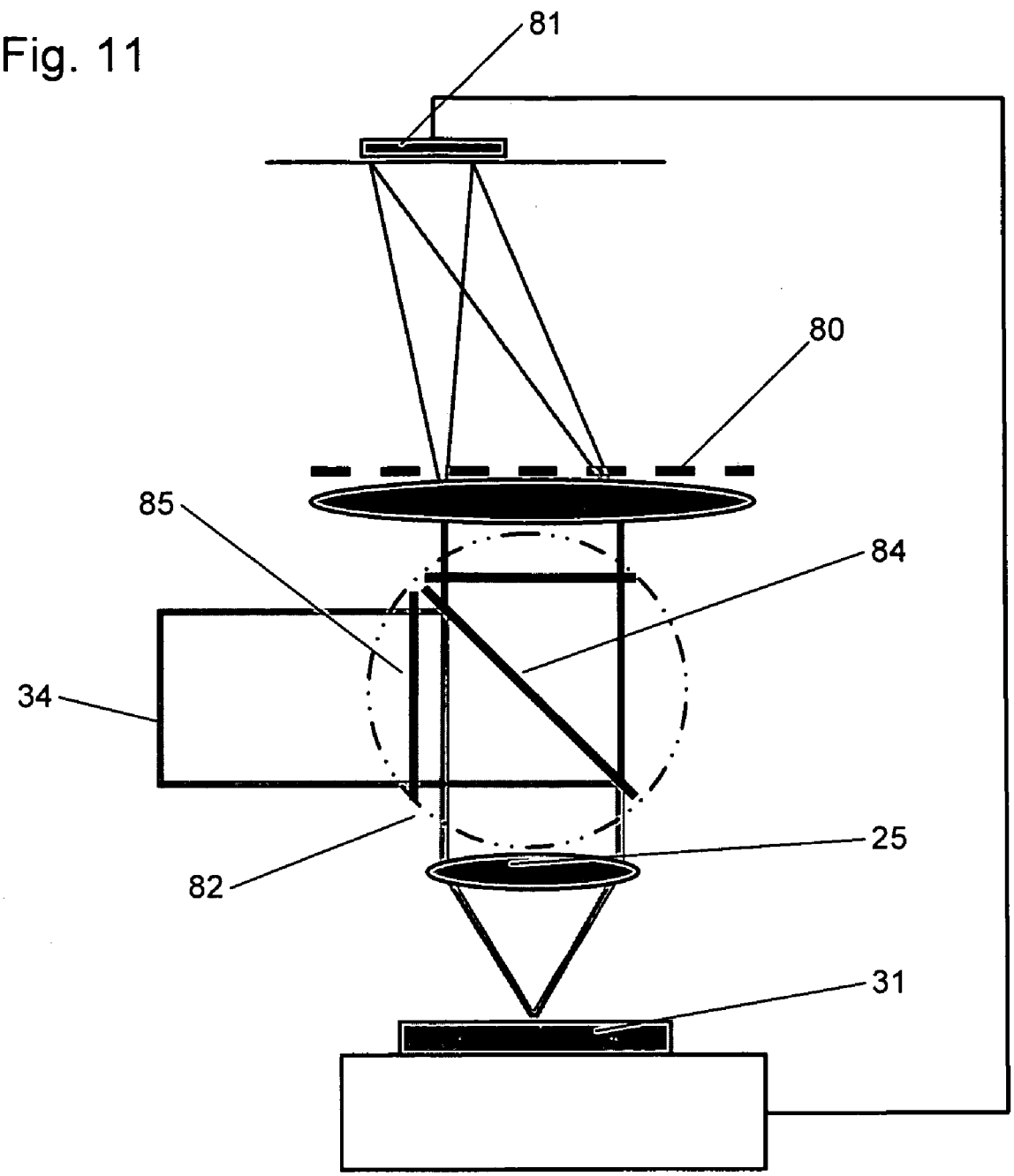
FIG. 11 is a diagram of an image scanning system that is configured to conduct multi-spectral fluorescence imaging.
Figure 12:
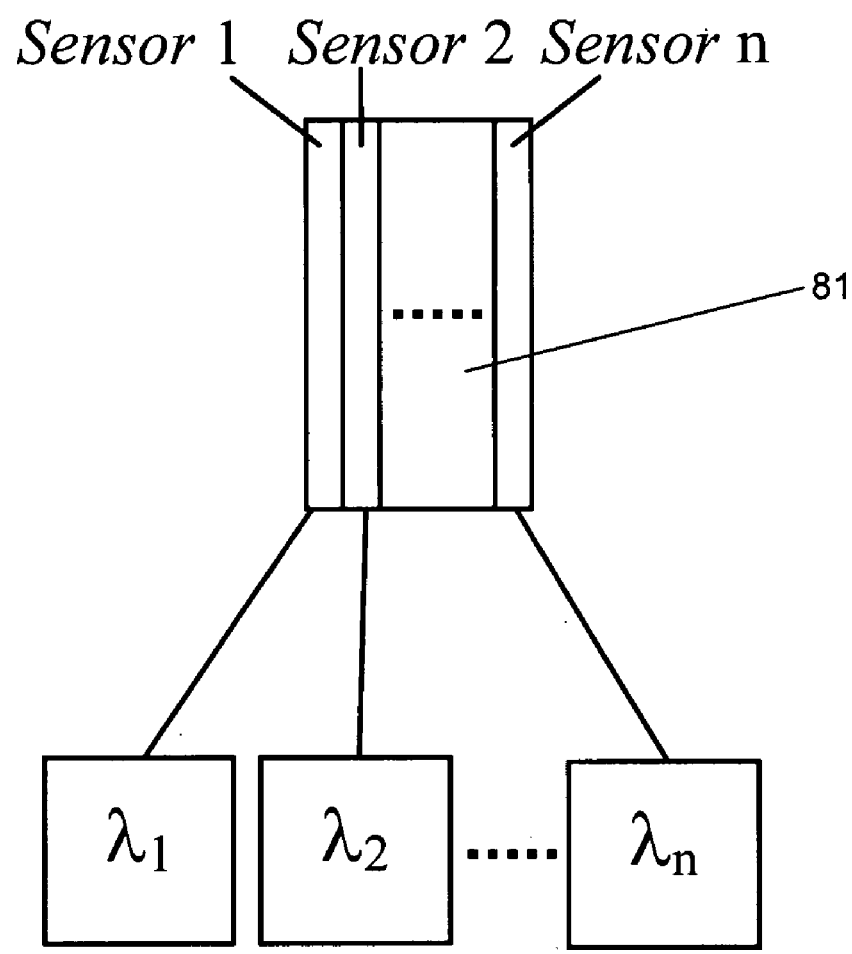
FIG. 12 is a block diagram of a line-scan imaging sensor.

According to another embodiment of the invention, the LIS 20 system architecture is configured to use parallel multi-spectral fluorescence imaging using line-scan imaging sensors. As shown in FIG. 11, line illumination 34 is used to excite fluorescent molecules in a full spectral range and a chromatic dispersion element 80 is used to spread the line fluorescence image 66 across multiple line-scan imaging sensors 81. The system can be implemented using side illumination or collinear illumination. According to this embodiment of the invention, a multi-band filter set 82 is used to excite and detect multiple fluorescent molecules. As represented in FIG. 12, each of the plurality of sensors 81 is mapped to a narrow band spectral range. The sensors 81 can be imaging sensors such as a linear line-scan CCD or a TDI line-scan CCD. Sensors are also referred to as detectors herein.

Figure 13:
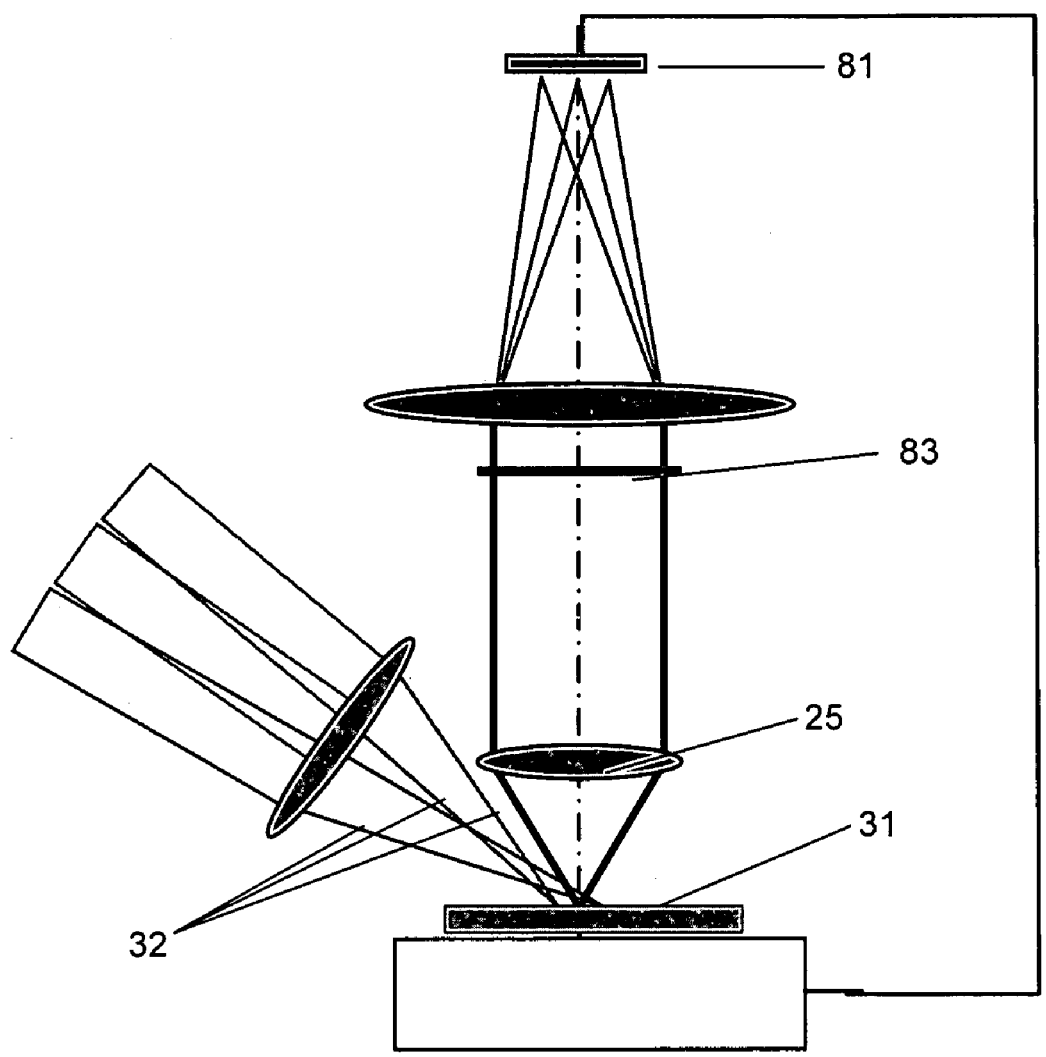
FIG. 13 is a diagram of an image scanning system that is configured to conduct multi-spectral fluorescence imaging.

As shown in FIG. 13, according to still another embodiment of the invention, the LIS 20 architecture can be configured to use a multi-line illumination technique. The system can be implemented using side illumination or collinear illumination. Here, each line 32 excites a sample region at a different wavelength, for example, to excite different fluorescent molecules. The resulting multi-line fluorescence image is collected by a detector 29 with multiple line-scan imaging sensors 81. Each sensor 81 generates the corresponded fluorescent image. Because the fluorescence with different spectral ranges is already spatially separated, no chromatic dispersion element 80 is required. A multi-notch filter 83 is used to effectively block residual Rayleigh and Raman scattered radiation.

Figure 14:
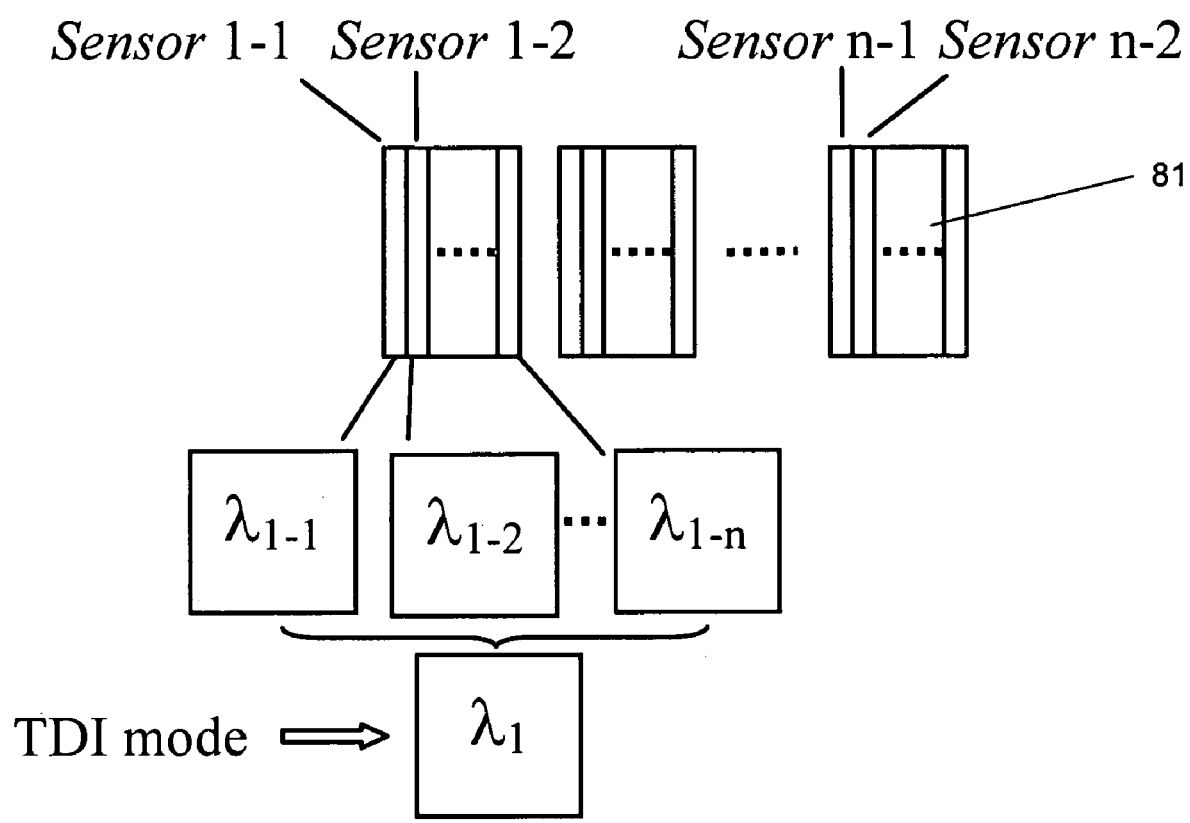
FIG. 14 is a block diagram of a line-scan imaging sensor.

Further, if a chromatic dispersion element is used in the system of FIG. 13, images with higher spectral resolution can be collected. As illustrated in FIG. 14, each sensor group 81 in the figure can also work in TDI mode to generate a single integrated image, which provides images with hierarchical spectral resolution.

The LIS 20 architecture can be designed to excite fluorescence of multiple dyes in different spectral ranges simultaneously. Exemplary architectures include a single line with multi-colors used in the system of FIG. 11 or spaced multi-lines with multi-colors used in the system of FIG. 13. The radiation source 21 can be a white light lamp with a multi-band excitation filter 86 or a combination of multiple lasers. The excitation filter 86 of the multi-band filter set 82 in the system of FIG. 11 is not required, for example, if the combination of multiple lasers is used as the radiation source 21. In addition, the illumination can be collinear illumination (illumination shares the same objective lens 25 as the collection) as shown in FIG. 12 or slide illumination (dark field) as shown in FIG. 14. A multi-band dichroic beam splitter 84 (shown in FIG. 11) can be used for the collinear illumination and omitted for the side illumination embodiment. Also as shown in FIG. 11, a multi-band emission filter 85 of the multi band filter set 82 can be used to selectively block excitation radiation while passing fluorescence bands. For illumination with multiple lasers, a multi-notch filter 83 can also be used to selectively block excitation radiation while passing fluorescence bands, which provides even more efficient florescence detection.

According to particular embodiments of the invention, emission filters 85 can be integrated with the image sensor 81. An exemplary orientation is shown in FIG. 15. A different orientation for blocking multi-band illumination and multiple laser illumination is shown in FIGS. 16(a) and 16(b) respectively.

An apparatus or method of the invention is particularly useful for obtaining an image of a 2-dimensional area of a sample. Thus, if desired, detection can be substantially restricted to obtaining an image in 2 of the 3 possible dimensions for a sample. Accordingly, an image of a surface for a sample of interest can be detected or imaged. A particularly relevant sample is a microarray. Using the invention the surface of a microarray can be detected or imaged to determine one or more property of the microarray. Exemplary properties of a microarray that can be detected include, but are not limited to, the presence or absence of a label, the location of a label at a particular location such as a location where a particular probe resides, or a specific characteristic of a label such as emission of radiation at a particular wavelength or wavelength range.

Detection of such properties for a microarray can be used to determine the presence or absence of a particular target molecule in a sample contacted with the microarray. This can be determined, for example, based on binding of a labeled target analyte to a particular probe of the microarray or due to a target-dependent modification of a particular probe to incorporate, remove or alter a label at the probe location. Any one of several assays can be used to identify or characterize targets using a microarray as described, for example, in U.S. Pat. App. Pub. Nos. 2003/0108867, 2003/0108900, 2003/0170684, 2003/0207295, or 2005/0181394, each of which is hereby incorporated by reference.

Exemplary labels that can be detected in accordance with the invention, for example, when present on a microarray include, but are not limited to, a chromophore; luminophore; fluorophore; optically encoded nanoparticles; particles encoded with a diffraction-grating; electrochemiluminescent label such as Ru(bpy)32+; or moiety that can be detected based on an optical characteristic. Fluorophores that are useful in the invention include, for example, fluorescent lanthanide complexes, including those of Europium and Terbium, fluorescein, rhodamine, tetramethylrhodamine, eosin, erythrosin, coumarin, methyl-coumarins, pyrene, Malacite green, Cy3, Cy5, stilbene, Lucifer Yellow, Cascade Blue™, Texas Red, alexa dyes, phycoerythin, bodipy, and others known in the art such as those described in Haugland, *Molecular Probes Handbook*, (Eugene, Oreg.) 6th Edition; The Synthegen catalog (Houston, Tex.), Lakowicz, *Principles of Fluorescence Spectroscopy, 2nd Ed.*, Plenum Press New York (1999), or WO 98/59066, each of which is hereby incorporated by reference.

Any of a variety of microarrays known in the art, including, for example, those set forth previously herein, can used as a sample in the invention. A typical microarray contains sites, sometimes referred to as features, each having a population of probes. The population of probes at each site typically is homogenous, having a single species of probe but in some embodiments the populations can each be heterogeneous. Sites or features of an array are typically discrete, being separated with spaces between each other. The size of the probe sites and/or spacing between the sites can vary such that arrays can be high density, medium density or lower density. High density arrays are characterized as having sites separated by less than about 15 μm. Medium density arrays have sites separated by about 15 to 30 μm, while low density arrays have sites separated by greater than 30 μm. An array useful in the invention can have sites that are separated by less than 100 μm, 50 μm, 10 μm, 5 μm, 1 μm or 0.5 μm. An apparatus or method of the invention can be used to image an array at a resolution sufficient to distinguish sites at the above densities or density ranges.

Although the invention has been exemplified above with regard to the use of a microarray as a sample, it will be understood that other samples having features or sites at the above densities can be imaged at the resolutions set forth above. Other exemplary samples include, but are not limited to, biological specimens such as cells or tissues, electronic chips such as those used in computer processors, or the like. A microarray or other sample can be placed in a sample region of an apparatus of the invention by being placed on a sample stage such as those described previously herein.

An apparatus of the invention can further include a processor, operably coupled to a rectangular detector array or otherwise configured to obtain data from the rectangular detector array, wherein the processor is configured to perform a plurality of functions on the image. The processor can include a conventional or general purpose computer system that is programmed with, or otherwise has access to, one or more program modules involved in the analysis of imaging data. Exemplary computer systems that are useful in the invention include, but are not limited to personal computer systems, such as those based on Intel®, IBM®, or Motorola® microprocessors; or work stations such as a SPARC® workstation or UNIX® workstation. Useful systems include those using the Microsoft® Windows®, UNIX or LINUX® operating system. The systems and methods described herein can also be implemented to run on client-server systems or wide-area networks such as the Internet.

The processor can be included in a computer system, configured to operate as either a client or server. The processor can execute instructions included in one or more program modules. Results from one or more program modules such as an image of a sample or sample region, or analysis of the sample or sample region can be reported to a user via a graphical user interface. For example, results can be reported via a monitor or printing device operably connected to the processor. Thus, an image of an array or other sample can be provided to a user via a graphical user interface.

According to certain aspects of the invention, several advantages are realized. The system of the present invention scans samples faster than other technologies and provides improved data quality at lower cost. Specifically, the readout rate of the present invention is increased by a factor of n as compared to conventional TDI systems. Confocality can be achieved in one or more axis. In addition, the present invention is less sensitive to optical alignment drifts.

Further, the present invention combines the advantages of simultaneous excitation/detection of multiple fluorescent molecules using multi-band filters and parallel readout of multiple line-scan imaging sensors on the same sample. The present invention can simultaneously generate multi-spectral fluorescence images in a fast speed. In particular embodiments, an apparatus of method of the invention can scan a sample at a rate of at least about 0.01 mm$^2$/sec. Depending upon the particular application of the invention faster scan rates can also be used including, for example, in terms of the area scanned, a rate of at least about 0.02 mm$^2$/sec, 0.05 mm$^2$/sec, 0.1 mm$^2$/sec, 1 mm$^2$/sec, 1.5 mm$^2$/sec, 5 mm$^2$/sec, 10 mm$^2$/sec, 50 mm$^2$/sec or 100 mm$^2$/sec or faster. If desired, for example, to reduce noise, scan rate can have an upper limit of about 0.05 mm$^2$/sec, 0.1 mm$^2$/sec, 1 mm$^2$/sec, 1.5 mm$^2$/sec, 5 mm$^2$/sec, 10 mm$^2$/sec, 50 mm$^2$/sec or 100 mm$^2$/sec. Scan rate can also be measured in terms of the rate of relative movement for an image and detector in the scan-axis (vertical) dimension and can be, for example, at least about 0.1 mm/sec, 0.5 mm/sec, 1 mm/sec, 10 mm/sec, or 100 mm/sec. Again, to reduce noise, scan rate can have an upper limit of about 0.5 mm/sec, 1 mm/sec, 10 mm/sec, or 100 mm/sec. In sum, the present invention can be used to build multi-spectral fluorescence imagers, which are more efficient and cost-effective than other imaging systems.

Throughout this application various publications, patents of patent applications have been referenced. The disclosure of these publications in their entireties is hereby incorporated by reference in this application in order to more fully describe the state of the art to which this invention pertains.

The term "comprising" is intended herein to be open-ended; including not only the recited elements, but further encompassing any additional elements.

Although the invention has been described with reference to the examples provided above, it should be understood that various modifications can be made without departing from the invention. Accordingly, the invention is limited only by the claims.

What is claimed is:

1. An imaging apparatus comprising:
   (a) a radiation source positioned to send excitation radiation to at least a portion of a sample region;
   (b) a rectangular detector array;
   (c) imaging optics positioned to direct a rectangular image of said portion to said rectangular detector array; and
   (d) a scanning device configured to scan said sample region in a scan-axis dimension, whereby the portion of said sample region that forms a rectangular image at said rectangular detector array is changed,
   wherein the shorter of the two rectangular dimensions for said rectangular detector array and the shorter of the two rectangular dimensions for said image are in said scan-axis dimension, and
   wherein said shorter of the two rectangular dimensions for said rectangular detector array is short enough to achieve confocality in a single axis of said rectangular detector array, wherein said single axis is said shorter of the two rectangular dimensions for said rectangular detector array.

2. The apparatus of claim 1, wherein the ratio of said shorter of the two rectangular dimensions for said rectangular detector array and the product of the Rayleigh resolution of the imaging optics multiplied by the magnification of the imaging optics is in the range of 0.1 to 10.

3. The apparatus of claim 1, further comprising a line generator positioned to receive excitation radiation from said radiation source and to send a radiation line to said sample region.

4. The apparatus of claim 3, further comprising an objective positioned to receive said radiation line therethrough to illuminate said sample region.

5. The apparatus of claim 4, wherein said imaging optics comprise said objective, wherein said objective is further positioned to collect radiation emanating from said sample region, wherein said radiation emanating from said sample region forms said rectangular image that is directed to said rectangular detector array.

6. The apparatus of claim 5, further comprising a beam splitter positioned to separate said radiation line from said radiation emanating from said sample region and to direct said radiation emanating from said sample region to the rectangular detector array.

7. The apparatus of claim 4, wherein said objective has an external pupil positioned to receive said radiation line therethrough to illuminate said sample region.

8. The apparatus of claim 4, further comprising a first expander positioned to receive excitation radiation from said radiation source and to send an expanded beam of said radiation to said line generator.

9. The apparatus of claim 8, further comprising a second expander positioned to receive said excitation radiation from said line generator and send an expanded beam of said radiation to said objective, wherein said second expander is further configured to decrease the field angle of said radiation line.

10. The apparatus of claim 4, wherein said objective has a property selected from the group consisting of color correction, high numerical aperture, telecentricity, and afocality at the backplane.

11. The apparatus of claim 3, wherein said line generator has a full fan angle of six degrees and is configured to receive an input beam having a diameter of at most 4 mm.

12. The apparatus of claim 3, wherein said line generator further comprises a cylindrical micro-lens array, one-dimensional diffuser having an angular uniformity, aspheric refractive lens, diffractive element or Powell lens.

13. The apparatus of claim 3, wherein said line generator further comprises a diffractive element to generate a diffraction-limited line with uniform intensity distribution.

14. The apparatus of claim 3, wherein the shorter of two rectangular dimensions for said radiation line is short enough to achieve confocality in a single axis of said rectangular detector array, wherein said single axis is said shorter of the two rectangular dimensions for said rectangular detector array.

15. The apparatus of claim 3, wherein the ratio of the shorter of two rectangular dimensions for said radiation line to the quotient of said shorter of the two rectangular dimensions divided by the magnification of the imaging optics is in the range of 0.1 to 10.

16. The apparatus of claim 3, wherein the ratio of the shorter of two rectangular dimensions for said radiation line to the Rayleigh resolution of the imaging optics is in the range of 0.1 to 10.

17. The apparatus of claim 3, wherein the ratio of the $1/e^2$ width of the shorter of two rectangular dimensions for said radiation line to the quotient of said shorter of the two rectangular dimensions for said rectangular detector array divided by the magnification of the imaging optics is in the range of 0.5 to 2.

18. The apparatus of claim 1, further comprising a projection lens positioned to collect radiation emanating from said sample region, wherein said radiation emanating from said sample region forms said rectangular image that is directed to said rectangular detector array.

19. The apparatus of claim 1, further comprising a band pass filter positioned to collect radiation emanating from said sample region, wherein said radiation emanating from said sample region forms said rectangular image that is directed to said rectangular detector array.

20. The apparatus of claim 1, further comprising an emission filter positioned to collect radiation emanating from said sample region, wherein said radiation emanating from said sample region forms said rectangular image that is directed to said rectangular detector array.

21. The apparatus of claim 1, further comprising a translation stage positioned to provide a sample to said sample region.

22. The apparatus of claim 21, wherein said translation stage is configured to move said sample in said scan-axis dimension.

23. The apparatus of claim 21, further comprising a microarray supported by said translation stage, whereby said array is provided to said sample region.

24. The apparatus of claim 1, wherein said rectangular detector array is configured for TDI (Time Delay Integration) operation.

25. The apparatus of claim 1, wherein said rectangular detector array comprises a line scan CCD camera, CMOS detector array, avalanche photodiode (APD) array, or Geiger-mode photon counter array.

26. The apparatus of claim 1, wherein the aspect ratio of said rectangular detector is greater than 20.

27. The apparatus of claim 1, wherein said radiation source comprises at least one laser.

28. The apparatus of claim 1, comprising multiple collection arms positioned to collect radiation emanating from said sample region, wherein said radiation emanating from said sample region forms multiple rectangular images that are directed to multiple rectangular detector arrays.

29. The apparatus of claim 1, wherein said apparatus is configured to obtain an image of said sample comprising a Rayleigh resolution between 0.2 and 10 micrometers.

30. A method of obtaining an image of a sample, comprising
(a) contacting at least a first portion of a sample with excitation radiation under conditions wherein radiation is emanated from said first portion;
(b) directing said radiation emanated from said first portion to form a rectangular image of said first portion at a rectangular detector array; and
(c) scanning said sample region in a scan-axis dimension, thereby repeating steps (a) and (b) to form a rectangular image of a second portion of said sample at said rectangular detector array,
wherein the shorter of the two rectangular dimensions for said rectangular detector array and the shorter of the two rectangular dimensions for said images are in said scan-axis dimension, and
wherein said shorter of the two rectangular dimensions for said rectangular detector array is short enough to achieve confocality in a single axis of said rectangular detector array, wherein said single axis is said shorter of the two rectangular dimensions for said rectangular detector array.

31. The method of claim 30, wherein the ratio of said shorter of the two rectangular dimensions for said rectangular detector array and the product of the Rayleigh resolution of said rectangular image multiplied by the magnification of the rectangular image is in the range of 0.1 to 10.

32. The method of claim 30, wherein said excitation radiation that contacts at least a portion of said sample comprises a radiation line.

33. The method of claim 32, wherein the shorter of two rectangular dimensions for said radiation line is short enough to achieve confocality in a single axis of said rectangular detector array, wherein said single axis is said shorter of the two rectangular dimensions for said rectangular detector array.

34. The method of claim 32, wherein the ratio of the shorter of two rectangular dimensions for said radiation line to the quotient of said shorter of the two rectangular dimensions for said rectangular detector array divided by the magnification is in the range of 0.1 to 10.

35. The method of claim 30, wherein the ratio of the $1/e^2$ width the shorter of two rectangular dimensions for said radiation line to the quotient of said shorter of the two rectangular dimensions for said rectangular detector array divided by the magnification is in the range of 0.5 to 2.

36. The method of claim 30, wherein said scanning said sample comprises moving said sample, thereby changing the relative positions of said rectangular image and said rectangular detector array in said scan-axis dimension.

37. The method of claim 30, wherein said scanning comprises TDI (Time Delay Integration).

38. The method of claim 30, wherein all pixel elements in the shorter of the two rectangular dimensions for said rectangular detector array are collected in a common bin and read out as a single value.

39. The method of claim 30, wherein said excitation radiation comprises radiation in a range selected from the group consisting of UV radiation, VIS radiation and IR radiation.

40. The method of claim 30, further comprising storing a data representation of said image of said sample in a computer readable memory.

41. The method of claim 40, further comprising displaying a graphical representation of said image of said sample on a monitor operably connected to said computer readable memory.

42. The method of claim 30, wherein said sample comprises a microarray having a plurality of individual sites.

43. The method of claim 42, wherein said individual sites are separated by a distance in the range of 0.1 to 50 micrometers.

44. The method of claim 43, further comprising distinguishing said individual sites.

45. The method of claim 30, wherein said image of said sample comprises a Rayleigh resolution between 0.2 and 10 micrometers.

46. A method of configuring a scanner to achieve confocality in a single axis, comprising,
(a) providing an apparatus comprising
(i) a radiation source positioned to send excitation radiation to at least a portion of a sample region;
(ii) a rectangular detector array;
(iii) imaging optics positioned to direct a rectangular image of said portion to said rectangular detector array; and
(iv) a scanning device configured to scan said sample region in a scan-axis dimension, whereby the portion of said sample region that forms a rectangular image at said rectangular detector array is changed,
wherein the shorter of the two rectangular dimensions for said rectangular detector array and the shorter of the two rectangular dimensions for said image are in said scan-axis dimension; and
(b) positioning said rectangular detector array or said imaging optics to restrict said shorter of the two rectangular dimensions for said rectangular detector array to be short enough to achieve confocality in a single axis of said rectangular detector array, wherein said single axis is said shorter of the two rectangular dimensions for said rectangular detector array.

* * * * *